(12) United States Patent
Parker

(10) Patent No.: US 8,388,644 B2
(45) Date of Patent: Mar. 5, 2013

(54) EMBOLIC PROTECTION DEVICE AND METHOD OF USE

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 622 days.

(21) Appl. No.: 12/345,127

(22) Filed: Dec. 29, 2008

(65) Prior Publication Data

US 2010/0168785 A1 Jul. 1, 2010

(51) Int. Cl.
*A61M 25/00* (2006.01)
(52) U.S. Cl. ......................................................... 606/200
(58) Field of Classification Search .................. 606/200, 606/191, 194, 198; 623/1.11, 1.12
See application file for complete search history.

(56) References Cited

U.S. PATENT DOCUMENTS

| | | | |
|---|---|---|---|
| 3,108,593 A | 10/1963 | Glassman |
| 3,334,629 A | 8/1967 | Cohn |
| 3,472,230 A | 10/1969 | Fogarty |
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |

(Continued)

FOREIGN PATENT DOCUMENTS

| DE | 3429850 A1 | 2/1986 |
|---|---|---|
| EP | 1127556 A2 | 8/2001 |

(Continued)

OTHER PUBLICATIONS

Rubicon Embolic Filter, The Next Generation of EM, Rubicon Medical, www.rubiconmed.com.

(Continued)

*Primary Examiner* — Ryan Severson
(74) *Attorney, Agent, or Firm* — Brinks hofer Gilson & Lione

(57) ABSTRACT

A medical device for embolic protection within a patient's body vessel is provided. The device includes inner and outer tubular members each having proximal and distal ends and a lumen formed through the proximal and distal ends. A flexible everting filter portion includes a body having a first end attached to the distal end of the inner tubular member and a second end attached to the distal end of the outer tubular member. The inner and outer tubular members are movable relative to one another to position the filter portion within the body vessel. The filter portion is movable from a collapsed, everted delivery and removal configuration to an expanded, generally non-everted deployed configuration. The filter portion expands radially outward to engage the filter body with the body vessel. The filter portion allows the passage of blood cells and prevents the passage of emboli or thrombi through the body vessel.

17 Claims, 4 Drawing Sheets

U.S. PATENT DOCUMENTS

| | | |
|---|---|---|
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallstén et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallstén et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A * | 8/1996 | Miller et al. ............... 606/200 |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |

| Patent No. | Kind | Date | Inventor |
|---|---|---|---|
| 6,083,239 | A | 7/2000 | Addis |
| 6,086,577 | A | 7/2000 | Ken et al. |
| 6,086,605 | A | 7/2000 | Barbut et al. |
| 6,093,199 | A | 7/2000 | Brown et al. |
| 6,096,053 | A | 8/2000 | Bates |
| 6,096,070 | A | 8/2000 | Ragheb et al. |
| 6,099,549 | A | 8/2000 | Bosma et al. |
| 6,106,497 | A | 8/2000 | Wang |
| 6,126,672 | A | 10/2000 | Berryman et al. |
| 6,126,673 | A | 10/2000 | Kim et al. |
| 6,129,739 | A | 10/2000 | Khosravi |
| 6,136,016 | A | 10/2000 | Barbut et al. |
| 6,146,396 | A | 11/2000 | Konya et al. |
| 6,146,404 | A | 11/2000 | Kim et al. |
| 6,152,931 | A | 11/2000 | Nadal et al. |
| 6,152,946 | A | 11/2000 | Broome et al. |
| 6,152,947 | A | 11/2000 | Ambrisco et al. |
| 6,156,061 | A | 12/2000 | Wallace et al. |
| 6,156,062 | A | 12/2000 | McGuinness |
| 6,159,230 | A | 12/2000 | Samuels |
| 6,165,179 | A | 12/2000 | Cathcart et al. |
| 6,165,198 | A | 12/2000 | McGurk et al. |
| 6,165,199 | A | 12/2000 | Barbut |
| 6,165,200 | A | 12/2000 | Tsugita et al. |
| 6,168,579 | B1 | 1/2001 | Tsugita et al. |
| 6,168,603 | B1 | 1/2001 | Leslie et al. |
| 6,168,610 | B1 | 1/2001 | Marin et al. |
| 6,168,622 | B1 | 1/2001 | Mazzocchi |
| 6,171,327 | B1 | 1/2001 | Daniel et al. |
| 6,171,328 | B1 | 1/2001 | Addis |
| 6,174,318 | B1 | 1/2001 | Bates et al. |
| 6,179,851 | B1 | 1/2001 | Barbut et al. |
| 6,179,859 | B1 | 1/2001 | Bates et al. |
| 6,179,860 | B1 | 1/2001 | Fulton, III et al. |
| 6,179,861 | B1 | 1/2001 | Khosravi et al. |
| 6,187,025 | B1 | 2/2001 | Machek |
| 6,193,739 | B1 | 2/2001 | Chevillon et al. |
| 6,203,561 | B1 | 3/2001 | Ramee et al. |
| 6,206,931 | B1 | 3/2001 | Cook et al. |
| 6,214,025 | B1 | 4/2001 | Thistle et al. |
| 6,214,026 | B1 | 4/2001 | Lepak et al. |
| 6,221,091 | B1 | 4/2001 | Khosravi |
| 6,224,620 | B1 | 5/2001 | Maahs |
| 6,231,588 | B1 | 5/2001 | Zadno-Azizi |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,241,746 | B1 | 6/2001 | Bosma et al. |
| 6,245,012 | B1 | 6/2001 | Kleshinski |
| 6,245,087 | B1 | 6/2001 | Addis |
| 6,245,088 | B1 | 6/2001 | Lowery |
| 6,245,089 | B1 | 6/2001 | Daniel et al. |
| 6,251,092 | B1 | 6/2001 | Qin et al. |
| 6,251,122 | B1 | 6/2001 | Tsukernik |
| 6,254,550 | B1 | 7/2001 | McNamara et al. |
| 6,254,633 | B1 | 7/2001 | Pinchuk et al. |
| 6,258,026 | B1 | 7/2001 | Ravenscroft et al. |
| 6,258,115 | B1 | 7/2001 | Dubrul |
| 6,258,120 | B1 | 7/2001 | McKenzie et al. |
| 6,261,305 | B1 | 7/2001 | Marotta et al. |
| 6,264,672 | B1 | 7/2001 | Fisher |
| 6,267,776 | B1 | 7/2001 | O'Connell |
| 6,267,777 | B1 | 7/2001 | Bosma et al. |
| 6,273,900 | B1 | 8/2001 | Nott et al. |
| 6,273,901 | B1 | 8/2001 | Whitcher et al. |
| 6,277,125 | B1 | 8/2001 | Barry et al. |
| 6,277,126 | B1 | 8/2001 | Barry et al. |
| 6,277,138 | B1 | 8/2001 | Levinson et al. |
| 6,277,139 | B1 | 8/2001 | Levinson et al. |
| 6,280,451 | B1 | 8/2001 | Bates et al. |
| 6,287,321 | B1 | 9/2001 | Jang |
| 6,290,710 | B1 | 9/2001 | Cryer et al. |
| 6,299,604 | B1 | 10/2001 | Ragheb et al. |
| 6,306,163 | B1 | 10/2001 | Fitz |
| 6,309,399 | B1 | 10/2001 | Barbut et al. |
| 6,312,444 | B1 | 11/2001 | Barbut |
| 6,319,268 | B1 | 11/2001 | Ambrisco et al. |
| 6,325,815 | B1 | 12/2001 | Kusleika et al. |
| 6,325,816 | B1 | 12/2001 | Fulton, III et al. |
| 6,328,755 | B1 | 12/2001 | Marshall |
| 6,331,183 | B1 | 12/2001 | Suon |
| 6,331,184 | B1 | 12/2001 | Abrams |
| 6,334,864 | B1 | 1/2002 | Amplatz et al. |
| 6,336,934 | B1 | 1/2002 | Gilson et al. |
| 6,338,739 | B1 | 1/2002 | Datta et al. |
| 6,340,364 | B2 | 1/2002 | Kanesaka |
| 6,342,062 | B1 | 1/2002 | Suon et al. |
| 6,342,063 | B1 | 1/2002 | DeVries et al. |
| 6,344,048 | B1 | 2/2002 | Chin et al. |
| 6,344,049 | B1 | 2/2002 | Levinson et al. |
| 6,346,116 | B1 | 2/2002 | Brooks et al. |
| 6,348,041 | B1 | 2/2002 | Klint |
| 6,348,063 | B1 | 2/2002 | Yassour et al. |
| 6,350,271 | B1 | 2/2002 | Kurz et al. |
| 6,355,051 | B1 | 3/2002 | Sisskind et al. |
| 6,358,228 | B1 | 3/2002 | Tubman et al. |
| 6,361,545 | B1 | 3/2002 | Macoviak et al. |
| 6,361,546 | B1 | 3/2002 | Khosravi |
| 6,361,547 | B1 | 3/2002 | Hieshima |
| 6,364,895 | B1 | 4/2002 | Greenhalgh |
| 6,364,896 | B1 | 4/2002 | Addis |
| 6,368,338 | B1 | 4/2002 | Konya et al. |
| 6,371,961 | B1 | 4/2002 | Osborne et al. |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,379,374 | B1 | 4/2002 | Hieshima et al. |
| 6,380,457 | B1 | 4/2002 | Yurek et al. |
| 6,383,146 | B1 | 5/2002 | Klint |
| 6,383,171 | B1 | 5/2002 | Gifford et al. |
| 6,383,174 | B1 | 5/2002 | Eder |
| 6,383,193 | B1 | 5/2002 | Cathcart et al. |
| 6,383,196 | B1 | 5/2002 | Leslie et al. |
| 6,383,205 | B1 | 5/2002 | Samson et al. |
| 6,383,206 | B1 | 5/2002 | Gillick et al. |
| 6,391,044 | B1 | 5/2002 | Yadav et al. |
| 6,391,045 | B1 | 5/2002 | Kim et al. |
| 6,391,052 | B2 | 5/2002 | Buirge et al. |
| 6,395,014 | B1 | 5/2002 | Macoviak et al. |
| 6,402,771 | B1 | 6/2002 | Palmer et al. |
| 6,402,772 | B1 | 6/2002 | Amplatz et al. |
| 6,409,742 | B1 | 6/2002 | Fulton, III et al. |
| 6,413,235 | B1 | 7/2002 | Parodi |
| 6,416,530 | B2 | 7/2002 | DeVries et al. |
| 6,419,686 | B1 | 7/2002 | McLeod et al. |
| 6,423,052 | B1 | 7/2002 | Escano |
| 6,423,086 | B1 | 7/2002 | Barbut et al. |
| 6,425,909 | B1 | 7/2002 | Dieck et al. |
| 6,428,557 | B1 | 8/2002 | Hilaire |
| 6,428,558 | B1 | 8/2002 | Jones et al. |
| 6,428,559 | B1 | 8/2002 | Johnson |
| 6,432,122 | B1 | 8/2002 | Gilson et al. |
| 6,436,112 | B2 | 8/2002 | Wensel et al. |
| 6,436,120 | B1 | 8/2002 | Meglin |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |
| 6,485,502 | B2 | 11/2002 | Don Michael et al. |
| 6,491,712 | B1 | 12/2002 | O'Connor |
| 6,494,895 | B2 | 12/2002 | Addis |
| 6,497,709 | B1 | 12/2002 | Heath |
| 6,499,487 | B1 | 12/2002 | McKenzie et al. |

| Patent No. | Date | Inventor |
|---|---|---|
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,204,847 B1 | 4/2007 | Gambale |

| | | | | | |
|---|---|---|---|---|---|
| 7,255,687 B2 | 8/2007 | Huang et al. | 2002/0103501 A1 | 8/2002 | Diaz et al. |
| 7,285,130 B2 | 10/2007 | Austin | 2002/0107541 A1 | 8/2002 | Vale et al. |
| 7,306,619 B1 | 12/2007 | Palmer | 2002/0111647 A1 | 8/2002 | Khairkhahan et al. |
| 7,371,248 B2 | 5/2008 | Dapolito et al. | 2002/0111648 A1 | 8/2002 | Kusleika et al. |
| 7,393,358 B2 | 7/2008 | Malewicz | 2002/0111649 A1 | 8/2002 | Russo et al. |
| 7,604,649 B2 | 10/2009 | McGuckin et al. | 2002/0116024 A1 | 8/2002 | Goldberg et al. |
| 7,666,216 B2 | 2/2010 | Hogendijk et al. | 2002/0120226 A1 | 8/2002 | Beck |
| 7,731,722 B2 | 6/2010 | Lavelle et al. | 2002/0120286 A1 | 8/2002 | DoBrava et al. |
| 7,766,934 B2 | 8/2010 | Pal et al. | 2002/0120287 A1 | 8/2002 | Huter |
| 2001/0000799 A1 | 5/2001 | Wessman et al. | 2002/0123720 A1 | 9/2002 | Kusleika et al. |
| 2001/0001817 A1 | 5/2001 | Humes | 2002/0123755 A1 | 9/2002 | Lowe et al. |
| 2001/0005789 A1 | 6/2001 | Root et al. | 2002/0123759 A1 | 9/2002 | Amplatz |
| 2001/0007947 A1 | 7/2001 | Kanesaka | 2002/0123766 A1 | 9/2002 | Seguin et al. |
| 2001/0011181 A1 | 8/2001 | DiMatteo | 2002/0128679 A1 | 9/2002 | Turovskiy et al. |
| 2001/0011182 A1 | 8/2001 | Dubrul et al. | 2002/0128680 A1 | 9/2002 | Pavlovic |
| 2001/0012951 A1 | 8/2001 | Bates et al. | 2002/0128681 A1 | 9/2002 | Broome et al. |
| 2001/0016755 A1 | 8/2001 | Addis | 2002/0133191 A1 | 9/2002 | Khosravi et al. |
| 2001/0020175 A1 | 9/2001 | Yassour et al. | 2002/0133192 A1 | 9/2002 | Kusleika et al. |
| 2001/0023358 A1 | 9/2001 | Tsukernik | 2002/0138094 A1 | 9/2002 | Borillo et al. |
| 2001/0025187 A1 | 9/2001 | Okada | 2002/0138095 A1 | 9/2002 | Mazzocchi et al. |
| 2001/0031980 A1 | 10/2001 | Wensel et al. | 2002/0138096 A1 | 9/2002 | Hieshima |
| 2001/0031981 A1 | 10/2001 | Evans et al. | 2002/0138097 A1 | 9/2002 | Ostrovsky et al. |
| 2001/0031982 A1 | 10/2001 | Peterson et al. | 2002/0143360 A1 | 10/2002 | Douk et al. |
| 2001/0039431 A1 | 11/2001 | DeVries et al. | 2002/0143361 A1 | 10/2002 | Douk et al. |
| 2001/0039432 A1 | 11/2001 | Whitcher et al. | 2002/0143362 A1 | 10/2002 | Macoviak et al. |
| 2001/0041908 A1 | 11/2001 | Levinson et al. | 2002/0151927 A1 | 10/2002 | Douk et al. |
| 2001/0041909 A1 | 11/2001 | Tsugita et al. | 2002/0151928 A1 | 10/2002 | Leslie et al. |
| 2001/0041928 A1 | 11/2001 | Pavcnik et al. | 2002/0156520 A1 | 10/2002 | Boylan et al. |
| 2001/0044632 A1 | 11/2001 | Daniel et al. | 2002/0161389 A1 | 10/2002 | Boyle et al. |
| 2001/0044634 A1 | 11/2001 | Don Michael et al. | 2002/0161390 A1 | 10/2002 | Mouw |
| 2001/0053921 A1 | 12/2001 | Jang | 2002/0161391 A1 | 10/2002 | Murphy et al. |
| 2002/0002383 A1 | 1/2002 | Sepetka et al. | 2002/0161392 A1 | 10/2002 | Dubrul |
| 2002/0002384 A1 | 1/2002 | Gilson et al. | 2002/0161393 A1 | 10/2002 | Demond et al. |
| 2002/0004667 A1 | 1/2002 | Adams et al. | 2002/0161394 A1 | 10/2002 | Macoviak et al. |
| 2002/0016564 A1 | 2/2002 | Courtney et al. | 2002/0161395 A1 | 10/2002 | Douk et al. |
| 2002/0016609 A1 | 2/2002 | Wensel et al. | 2002/0161396 A1 | 10/2002 | Jang et al. |
| 2002/0022858 A1 | 2/2002 | Demond et al. | 2002/0165557 A1 | 11/2002 | McAlister |
| 2002/0022859 A1 | 2/2002 | Hogendijk | 2002/0165573 A1 | 11/2002 | Barbut |
| 2002/0026211 A1 | 2/2002 | Khosravi et al. | 2002/0165576 A1 | 11/2002 | Boyle et al. |
| 2002/0026212 A1 | 2/2002 | Wholey et al. | 2002/0165598 A1 | 11/2002 | Wahr et al. |
| 2002/0026213 A1 | 2/2002 | Gilson et al. | 2002/0169472 A1 | 11/2002 | Douk et al. |
| 2002/0032460 A1 | 3/2002 | Kusleika et al. | 2002/0169474 A1 | 11/2002 | Kusleika et al. |
| 2002/0032461 A1 | 3/2002 | Marshall | 2002/0173815 A1 | 11/2002 | Hogendijk et al. |
| 2002/0042626 A1 | 4/2002 | Hanson et al. | 2002/0173819 A1 | 11/2002 | Leeflang et al. |
| 2002/0042627 A1 | 4/2002 | Brady et al. | 2002/0177872 A1 | 11/2002 | Papp et al. |
| 2002/0045915 A1 | 4/2002 | Balceta et al. | 2002/0177899 A1 | 11/2002 | Eum et al. |
| 2002/0045916 A1 | 4/2002 | Gray et al. | 2002/0183781 A1 | 12/2002 | Casey et al. |
| 2002/0045918 A1 | 4/2002 | Suon et al. | 2002/0183782 A1 | 12/2002 | Tsugita et al. |
| 2002/0049452 A1 | 4/2002 | Kurz et al. | 2002/0183783 A1 | 12/2002 | Shadduck |
| 2002/0049468 A1 | 4/2002 | Streeter et al. | 2002/0188313 A1 | 12/2002 | Johnson et al. |
| 2002/0052627 A1 | 5/2002 | Boylan et al. | 2002/0188314 A1 | 12/2002 | Anderson et al. |
| 2002/0058904 A1 | 5/2002 | Boock et al. | 2002/0193824 A1 | 12/2002 | Boylan et al. |
| 2002/0058911 A1 | 5/2002 | Gilson et al. | 2002/0193825 A1 | 12/2002 | McGuckin et al. |
| 2002/0058963 A1 | 5/2002 | Vale et al. | 2002/0193826 A1 | 12/2002 | McGuckin et al. |
| 2002/0058964 A1 | 5/2002 | Addis | 2002/0193827 A1 | 12/2002 | McGuckin et al. |
| 2002/0062133 A1 | 5/2002 | Gilson et al. | 2002/0193828 A1 | 12/2002 | Griffin et al. |
| 2002/0062134 A1 | 5/2002 | Barbut et al. | 2002/0198561 A1 | 12/2002 | Amplatz |
| 2002/0062135 A1 | 5/2002 | Mazzocchi et al. | 2003/0004536 A1 | 1/2003 | Boylan et al. |
| 2002/0065507 A1 | 5/2002 | Zadno-Azizi | 2003/0004537 A1 | 1/2003 | Boyle et al. |
| 2002/0068954 A1 | 6/2002 | Foster | 2003/0004538 A1 | 1/2003 | Secrest et al. |
| 2002/0068955 A1 | 6/2002 | Khosravi | 2003/0004539 A1 | 1/2003 | Linder et al. |
| 2002/0072764 A1 | 6/2002 | Sepetka et al. | 2003/0004540 A1 | 1/2003 | Linder et al. |
| 2002/0072765 A1 | 6/2002 | Mazzocchi et al. | 2003/0004541 A1 | 1/2003 | Linder et al. |
| 2002/0077596 A1 | 6/2002 | McKenzie et al. | 2003/0004542 A1 | 1/2003 | Wensel et al. |
| 2002/0082558 A1 | 6/2002 | Samson et al. | 2003/0009146 A1 | 1/2003 | Muni et al. |
| 2002/0082639 A1 | 6/2002 | Broome et al. | 2003/0009189 A1 | 1/2003 | Gilson et al. |
| 2002/0087187 A1 | 7/2002 | Mazzocchi et al. | 2003/0009190 A1 | 1/2003 | Kletschka et al. |
| 2002/0090389 A1 | 7/2002 | Humes et al. | 2003/0009191 A1 | 1/2003 | Wensel et al. |
| 2002/0091407 A1 | 7/2002 | Zadno-Azizi et al. | 2003/0014072 A1 | 1/2003 | Wensel et al. |
| 2002/0091408 A1 | 7/2002 | Sutton et al. | 2003/0018354 A1 | 1/2003 | Roth et al. |
| 2002/0091409 A1 | 7/2002 | Sutton et al. | 2003/0018355 A1 | 1/2003 | Goto et al. |
| 2002/0095170 A1 | 7/2002 | Krolik et al. | 2003/0023263 A1 | 1/2003 | Krolik et al. |
| 2002/0095171 A1 | 7/2002 | Belef | 2003/0023264 A1 | 1/2003 | Dieck et al. |
| 2002/0095172 A1 | 7/2002 | Mazzocchi et al. | 2003/0023265 A1 | 1/2003 | Forber |
| 2002/0095173 A1 | 7/2002 | Mazzocchi et al. | 2003/0032976 A1 | 2/2003 | Boucek |
| 2002/0095174 A1 | 7/2002 | Tsugita et al. | 2003/0032977 A1 | 2/2003 | Brady |
| 2002/0099405 A1 | 7/2002 | Yurek et al. | 2003/0040772 A1 | 2/2003 | Hyodoh et al. |
| 2002/0099407 A1 | 7/2002 | Becker et al. | 2003/0045897 A1 | 3/2003 | Huter et al. |
| 2002/0099435 A1 | 7/2002 | Stinson | 2003/0045898 A1 | 3/2003 | Harrison et al. |

| | | | | | |
|---|---|---|---|---|---|
| 2003/0050662 A1 | 3/2003 | Don Michael | 2003/0181942 A1 | 9/2003 | Sutton et al. |
| 2003/0055452 A1 | 3/2003 | Joergensen et al. | 2003/0181943 A1 | 9/2003 | Daniel et al. |
| 2003/0055480 A1 | 3/2003 | Fischell et al. | 2003/0187474 A1 | 10/2003 | Keegan et al. |
| 2003/0060843 A1 | 3/2003 | Boucher | 2003/0187475 A1 | 10/2003 | Tsugita et al. |
| 2003/0060844 A1 | 3/2003 | Borillo et al. | 2003/0187495 A1 | 10/2003 | Cully et al. |
| 2003/0065354 A1 | 4/2003 | Boyle et al. | 2003/0191492 A1 | 10/2003 | Gellman et al. |
| 2003/0065355 A1 | 4/2003 | Weber | 2003/0191493 A1 | 10/2003 | Epstein et al. |
| 2003/0065356 A1 | 4/2003 | Tsugita et al. | 2003/0195554 A1 | 10/2003 | Shen et al. |
| 2003/0069596 A1 | 4/2003 | Eskuri | 2003/0195555 A1 | 10/2003 | Khairkhahan et al. |
| 2003/0073979 A1 | 4/2003 | Naimark et al. | 2003/0195556 A1 | 10/2003 | Stack et al. |
| 2003/0074019 A1 | 4/2003 | Gray et al. | 2003/0199819 A1 | 10/2003 | Beck |
| 2003/0074054 A1 | 4/2003 | Duerig et al. | 2003/0199917 A1 | 10/2003 | Knudson et al. |
| 2003/0078614 A1 | 4/2003 | Salahieh et al. | 2003/0199918 A1 | 10/2003 | Patel et al. |
| 2003/0083608 A1 | 5/2003 | Evans et al. | 2003/0199919 A1 | 10/2003 | Palmer et al. |
| 2003/0083692 A1 | 5/2003 | Vrba et al. | 2003/0199920 A1 | 10/2003 | Boylan et al. |
| 2003/0083693 A1 | 5/2003 | Daniel et al. | 2003/0199921 A1 | 10/2003 | Palmer et al. |
| 2003/0088211 A1 | 5/2003 | Anderson et al. | 2003/0204168 A1 | 10/2003 | Bosma et al. |
| 2003/0088266 A1 | 5/2003 | Bowlin | 2003/0204202 A1 | 10/2003 | Palmer et al. |
| 2003/0093110 A1 | 5/2003 | Vale | 2003/0204203 A1 | 10/2003 | Khairkhahan et al. |
| 2003/0093112 A1 | 5/2003 | Addis | 2003/0208222 A1 | 11/2003 | Zadno-Azizi |
| 2003/0097094 A1 | 5/2003 | Ouriel et al. | 2003/0208224 A1 | 11/2003 | Broome |
| 2003/0097145 A1 | 5/2003 | Goldberg et al. | 2003/0208225 A1 | 11/2003 | Goll et al. |
| 2003/0100917 A1 | 5/2003 | Boyle et al. | 2003/0208226 A1 | 11/2003 | Bruckheimer et al. |
| 2003/0100918 A1 | 5/2003 | Duane | 2003/0208227 A1 | 11/2003 | Thomas |
| 2003/0100919 A1 | 5/2003 | Hopkins et al. | 2003/0208228 A1 | 11/2003 | Gilson et al. |
| 2003/0105472 A1 | 6/2003 | McAlister | 2003/0208229 A1 | 11/2003 | Kletschka |
| 2003/0105484 A1 | 6/2003 | Boyle et al. | 2003/0208253 A1 | 11/2003 | Beyer et al. |
| 2003/0105486 A1 | 6/2003 | Murphy et al. | 2003/0212428 A1 | 11/2003 | Richter |
| 2003/0109824 A1 | 6/2003 | Anderson et al. | 2003/0212429 A1 | 11/2003 | Keegan et al. |
| 2003/0109897 A1 | 6/2003 | Walak et al. | 2003/0212431 A1 | 11/2003 | Brady et al. |
| 2003/0109916 A1 | 6/2003 | Don Michael | 2003/0212432 A1 | 11/2003 | Khairkhahan et al. |
| 2003/0114879 A1 | 6/2003 | Euteneuer et al. | 2003/0212433 A1 | 11/2003 | Ambrisco et al. |
| 2003/0114880 A1 | 6/2003 | Hansen et al. | 2003/0212434 A1 | 11/2003 | Thielen |
| 2003/0120303 A1 | 6/2003 | Boyle et al. | 2003/0216774 A1 | 11/2003 | Larson |
| 2003/0120304 A1 | 6/2003 | Kaganov et al. | 2003/0220665 A1 | 11/2003 | Eskuri et al. |
| 2003/0125764 A1 | 7/2003 | Brady et al. | 2003/0220667 A1 | 11/2003 | Van der Burg et al. |
| 2003/0125765 A1 | 7/2003 | Blackledge et al. | 2003/0225418 A1 | 12/2003 | Esksuri et al. |
| 2003/0130680 A1 | 7/2003 | Russell | 2003/0225435 A1 | 12/2003 | Hunter et al. |
| 2003/0130681 A1 | 7/2003 | Ungs | 2003/0229374 A1 | 12/2003 | Brady et al. |
| 2003/0130682 A1 | 7/2003 | Broome et al. | 2003/0233117 A1 | 12/2003 | Adams et al. |
| 2003/0130684 A1 | 7/2003 | Brady et al. | 2004/0006364 A1 | 1/2004 | Ladd |
| 2003/0130685 A1 | 7/2003 | Daniel et al. | 2004/0006365 A1 | 1/2004 | Brady et al. |
| 2003/0130686 A1 | 7/2003 | Daniel et al. | 2004/0006370 A1 | 1/2004 | Tsugita |
| 2003/0130687 A1 | 7/2003 | Daniel et al. | 2004/0015152 A1 | 1/2004 | Day |
| 2003/0130688 A1 | 7/2003 | Daniel et al. | 2004/0039412 A1 | 2/2004 | Isshiki et al. |
| 2003/0135232 A1 | 7/2003 | Douk et al. | 2004/0049226 A1 | 3/2004 | Keegan et al. |
| 2003/0135233 A1 | 7/2003 | Bates et al. | 2004/0054394 A1 | 3/2004 | Lee |
| 2003/0139764 A1 | 7/2003 | Levinson et al. | 2004/0054395 A1 | 3/2004 | Lee et al. |
| 2003/0139765 A1 | 7/2003 | Patel et al. | 2004/0059372 A1 | 3/2004 | Tsugita |
| 2003/0144685 A1 | 7/2003 | Boyle et al. | 2004/0064067 A1 | 4/2004 | Ward |
| 2003/0144686 A1 | 7/2003 | Martinez et al. | 2004/0064179 A1 | 4/2004 | Linder et al. |
| 2003/0144687 A1 | 7/2003 | Brady et al. | 2004/0068271 A1 | 4/2004 | McAlister |
| 2003/0144688 A1 | 7/2003 | Brady et al. | 2004/0078044 A1 | 4/2004 | Kear |
| 2003/0144689 A1 | 7/2003 | Brady et al. | 2004/0082962 A1 | 4/2004 | Demarais et al. |
| 2003/0150821 A1 | 8/2003 | Bates et al. | 2004/0088038 A1 | 5/2004 | Dehnad et al. |
| 2003/0153935 A1 | 8/2003 | Mialhe | 2004/0093009 A1 | 5/2004 | Denison et al. |
| 2003/0153942 A1 | 8/2003 | Wang et al. | 2004/0093012 A1 | 5/2004 | Cully et al. |
| 2003/0153943 A1 | 8/2003 | Michael et al. | 2004/0093016 A1 | 5/2004 | Root et al. |
| 2003/0153944 A1 | 8/2003 | Phung et al. | 2004/0093059 A1 | 5/2004 | Lee et al. |
| 2003/0153945 A1 | 8/2003 | Patel et al. | 2004/0098022 A1 | 5/2004 | Barone |
| 2003/0158518 A1 | 8/2003 | Schonholz et al. | 2004/0098026 A1 | 5/2004 | Joergensen et al. |
| 2003/0158574 A1 | 8/2003 | Esch et al. | 2004/0098033 A1 | 5/2004 | Leeflang et al. |
| 2003/0158575 A1 | 8/2003 | Boylan et al. | 2004/0098112 A1 | 5/2004 | DiMatteo et al. |
| 2003/0163158 A1 | 8/2003 | White | 2004/0102719 A1 | 5/2004 | Keith et al. |
| 2003/0163159 A1 | 8/2003 | Patel et al. | 2004/0106944 A1 | 6/2004 | Daniel et al. |
| 2003/0167068 A1 | 9/2003 | Amplatz | 2004/0116831 A1 | 6/2004 | Vrba |
| 2003/0167069 A1 | 9/2003 | Gonzales et al. | 2004/0133232 A1 | 7/2004 | Rosenbluth et al. |
| 2003/0171769 A1 | 9/2003 | Barbut | 2004/0138696 A1 | 7/2004 | Drasler et al. |
| 2003/0171770 A1 | 9/2003 | Kusleika et al. | 2004/0153118 A1 | 8/2004 | Clubb et al. |
| 2003/0171771 A1 | 9/2003 | Anderson et al. | 2004/0158278 A1 | 8/2004 | Becker et al. |
| 2003/0171772 A1 | 9/2003 | Amplatz | 2004/0162576 A1 | 8/2004 | Barbut et al. |
| 2003/0171800 A1 | 9/2003 | Bicek et al. | 2004/0164030 A1 | 8/2004 | Lowe et al. |
| 2003/0171803 A1 | 9/2003 | Shimon | 2004/0167567 A1 | 8/2004 | Cano et al. |
| 2003/0176884 A1 | 9/2003 | Berrada et al. | 2004/0176794 A1 | 9/2004 | Khosravi |
| 2003/0176885 A1 | 9/2003 | Broome et al. | 2004/0176833 A1 | 9/2004 | Pavcnik et al. |
| 2003/0176886 A1 | 9/2003 | Wholey et al. | 2004/0199203 A1 | 10/2004 | Oslund et al. |
| 2003/0176887 A1 | 9/2003 | Petersen | 2004/0204737 A1 | 10/2004 | Boismier et al. |
| 2003/0176888 A1 | 9/2003 | O'Connell | 2004/0215322 A1 | 10/2004 | Kerr |
| 2003/0176889 A1 | 9/2003 | Boyle et al. | 2004/0225321 A1 | 11/2004 | Krolik et al. |

| | | |
|---|---|---|
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1* | 6/2007 | Coughlin ............... 606/200 |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82, 2727 (2003), pp. 2727.

* cited by examiner

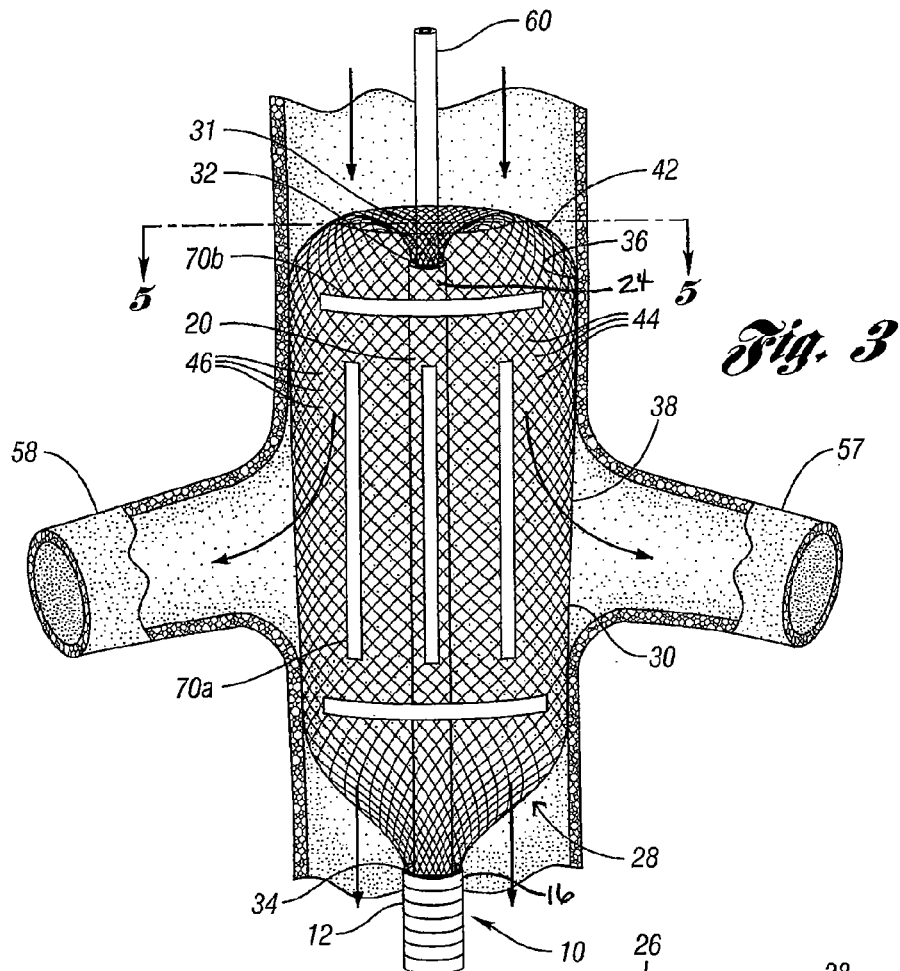
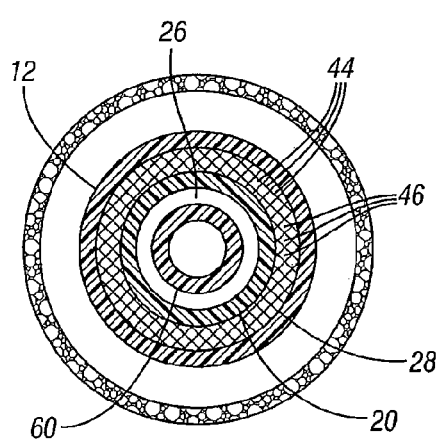
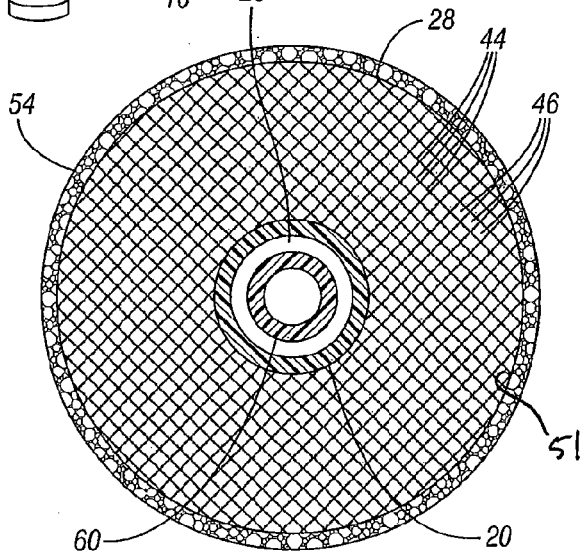
Fig. 3
Fig. 4
Fig. 5

EMBOLIC PROTECTION DEVICE AND METHOD OF USE

BACKGROUND OF THE INVENTION

1. Field of Invention

The present invention relates to medical devices. More particularly, the invention relates to a medical device for embolic protection.

2. Background

With the continuing advance of medical techniques, interventional procedures are more commonly being used to actively treat stenosis, occlusions, lesions, or other defects within a patient's blood vessels. Often the treated regions are in the coronary, carotid, renal, peripheral, cerebral and other blood vessels. For example, atherectomy or thrombectomy devices can be used to remove atheroma or thrombus. Another procedure for treating an occluded or stenosed blood vessel is angioplasty. During angioplasty, an inflatable balloon is introduced into the occluded region. The balloon is inflated, pushing against the plaque or other material of the stenosed region and increasing the intralumenal diameter of the vessel. As the balloon presses against the material, portions of the material may inadvertently break free from the plaque deposit. These emboli may flow downstream where they may block more distal and smaller blood vessel restricting blood flow to a vital organ, such as the brain. Consequences of embolization include stroke, diminished renal function, and impairment of peripheral circulation possibly leading to pain and amputation.

To prevent the risk of damage from emboli, various filtering devices have been proposed. Such devices typically have elements that form legs or a mesh that would capture embolic material, but allow blood cells to flow between the elements. Capturing the emboli in the filter device prevents the material from being lodged downstream in a smaller blood vessel. The filter may then be removed along with the embolic material after the procedure has been performed and the risk from emboli has decreased.

Many challenges exist with filtering devices. Often it is desirable to deploy filter devices, from the proximal side of a stenosis. Therefore, the profile of the filtering device should be significantly smaller than the opening in the stenosed vessel. If the profile of the filtering device is not significantly smaller than the opening, there is an increased risk of dislodging emboli during insertion of the device. Further, if the filter portion is not held against the inside of the vessel wall, there is a risk that embolic material may pass between the filter and the vessel wall. In addition, if the filtering device becomes filled with particles blood flow through the filtering device may be compromised.

In view of the above, it is apparent that there exists a need for an improved medical device for embolic protection.

BRIEF SUMMARY OF THE INVENTION

The present invention provides an improved medical device for embolic protection and an improved method of embolic protection during a medical procedure, the medical device being applicable to blood vessel, renal, and other applications similar in nature.

In one embodiment, the medical device includes outer and inner catheters and a flexible filter portion attached to both the outer and inner catheters. The outer catheter includes a proximal end and a distal end. An outer lumen is formed through the proximal and distal ends of the outer catheter, defining a proximal opening at the proximal end and a distal opening at the distal end. The inner catheter is movable within the outer catheter and includes a proximal end and a distal end. An inner lumen is formed through the proximal and distal ends of the inner catheter, defining a proximal opening at the proximal end and a distal opening at the distal end.

In this embodiment, the flexible filter portion includes a body extending from a first end to a second end. The first end of the filter portion is attached to the distal end of the inner catheter and the second end of the filter portion is attached to the distal end of the outer catheter. The outer and inner catheters are movable relative to one another to move the filter portion between a collapsed state for delivery and removal of the device and an expanded state for engaging the filter body with a body vessel wall. The distal end of the inner catheter is arranged proximal to the distal end of the outer catheter such that the filter body is everted and defines an everted distal cavity within the distal end of the outer catheter in the collapsed state. The distal end of the inner catheter is movable distal to the distal end of the outer catheter such that the filter body is generally non-everted and defines a cylindrical body extending distally from the distal end of the outer catheter in the expanded state. In both the collapsed and expanded states, the distal ends of the outer catheter and the inner catheter are longitudinally separated by approximately the length of the filter body.

In another embodiment, the medical device includes an elongate outer tubular member and an elongate inner tubular member movable within the outer tubular member. Each of the outer and inner tubular members have a proximal end and a distal end and a lumen formed through the proximal and distal ends defining a proximal opening at the proximal end and a distal opening at the distal end. The medical device further includes a flexible everting filter portion including a body extending from a first end to a second end. The first end is attached to the distal end of the inner tubular member and the second end is attached to the distal end of the outer tubular member. The filter portion is movable between a collapsed delivery and removal configuration and an expanded deployed configuration. The inner and outer tubular members are movable relative to one another to extend the filter portion from the outer tubular member. The filter portion is biased to expand radially outward to engage the filter body with an enclosing body vessel wall in the expanded configuration.

The present invention also includes an improved method of embolic protection during a medical procedure in a patient's body vessel. The method comprises inserting a medical device into an operative position within the body vessel. The medical device includes an outer tubular member and an inner tubular member movable within the outer tubular member. Each of the outer and inner tubular members has a proximal end and a distal end. A lumen is formed through the proximal and distal ends of each of the outer and inner tubular members, defining a proximal opening at the proximal end and a distal opening at the distal end.

In this embodiment, the medical device further includes a flexible filter portion having a body extending from a first end to a second end. The first end of the filter portion is attached to the distal end of the inner tubular member and the second end of the filter portion is attached to the distal end of the outer tubular member. The filter portion is compressed in an everted state within the distal end of the outer tubular member, defining a collapsed configuration during insertion of the medical device.

The method of embolic protection further includes deploying the filter portion within the body vessel to an expanded configuration in which the filter portion extends from the outer tubular member and is biased to expand radially outward to engage the filter body with an enclosing body vessel wall. After the filter portion is deployed within the body vessel, a medical procedure is performed upstream of the filter portion. This includes inserting an elongate medical instrument through the lumen of the inner tubular member into the body vessel adjacent a treatment site and performing the medical procedure. After the medical procedure has been performed, the elongate medical instrument is removed from within the inner tubular member and the body vessel. The inner and outer tubular members are movable relative to one another to position the filter portion back into the collapsed state and the medical device is removed from within the body vessel.

Further objects, features, and advantages of the present invention will become apparent from consideration of the following description and the appended claims when taken in connection with the accompanying drawings.

BRIEF DESCRIPTION OF THE DRAWINGS

FIG. 3 is a cutaway perspective view of an embolic protection device deployed within an abdominal aorta in the general vicinity of the renal arteries in accordance with an embodiment of the present invention;

FIG. 4 is a cross-sectional view taken along line 4-4 of FIG. 2;

FIG. 5 is a cross-sectional view taken along line 5-5 of FIG. 3; and

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

Figure 1:
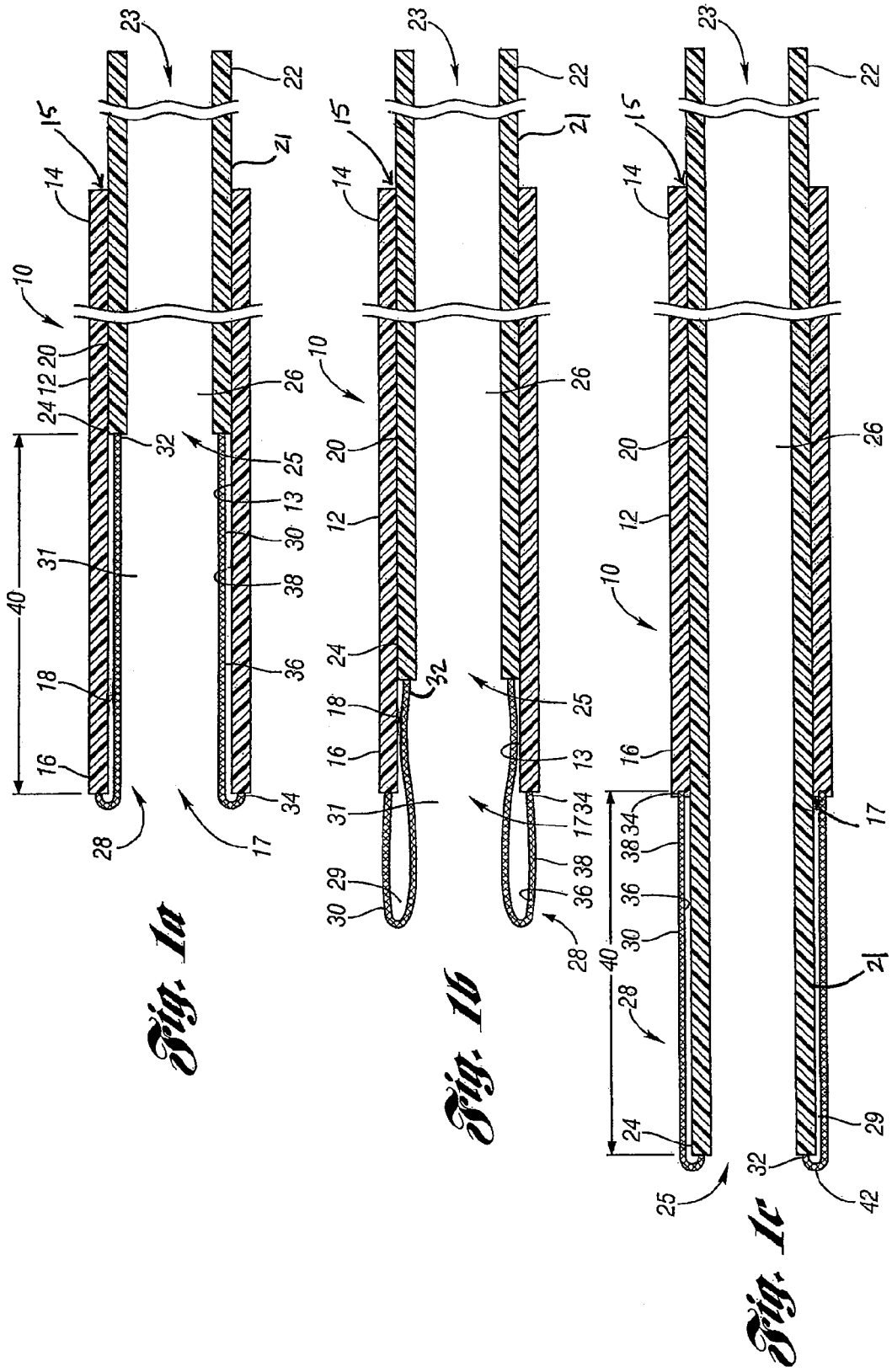
FIG. 1a is a side cross-sectional view of an embolic protection device in accordance with an embodiment of the present invention, in an everted state for delivery or removal of the device within a patient's body vessel.
FIG. 1b is a side cross-sectional view of the embolic protection device of FIG. 1a, in a partially everted state.
FIG. 1c is a side cross-sectional view of the embolic protection device of FIG. 1a, in a generally non-everted state.

Referring now to FIGS. 1a-c, an embolic protection device embodying the principles of the present invention is denoted by reference numeral 10. The device 10 includes an outer catheter 12, an inner catheter 20, and a flexible filter portion 28. The term catheter as used herein refers to any catheter, cannula, tube, sheath, or the like which is inserted into a patient's vascular system for delivery or withdrawal of fluids and/or introduction of catheters and the like. As illustrated in FIGS. 1a-c, the outer catheter 12 has a proximal end 14 and a distal end 16 and a lumen 18 formed through the proximal and distal ends 14, 16, defining a proximal opening 15 at the proximal end 14 and a distal opening 17 at the distal end 16. The inner catheter 20 has a proximal end 22 and a distal end 24 and a lumen 26 formed through the proximal and distal ends 24, 26, defining a proximal opening 23 at the proximal end 22 and a distal opening 25 at the distal end 24.

Figure 2:
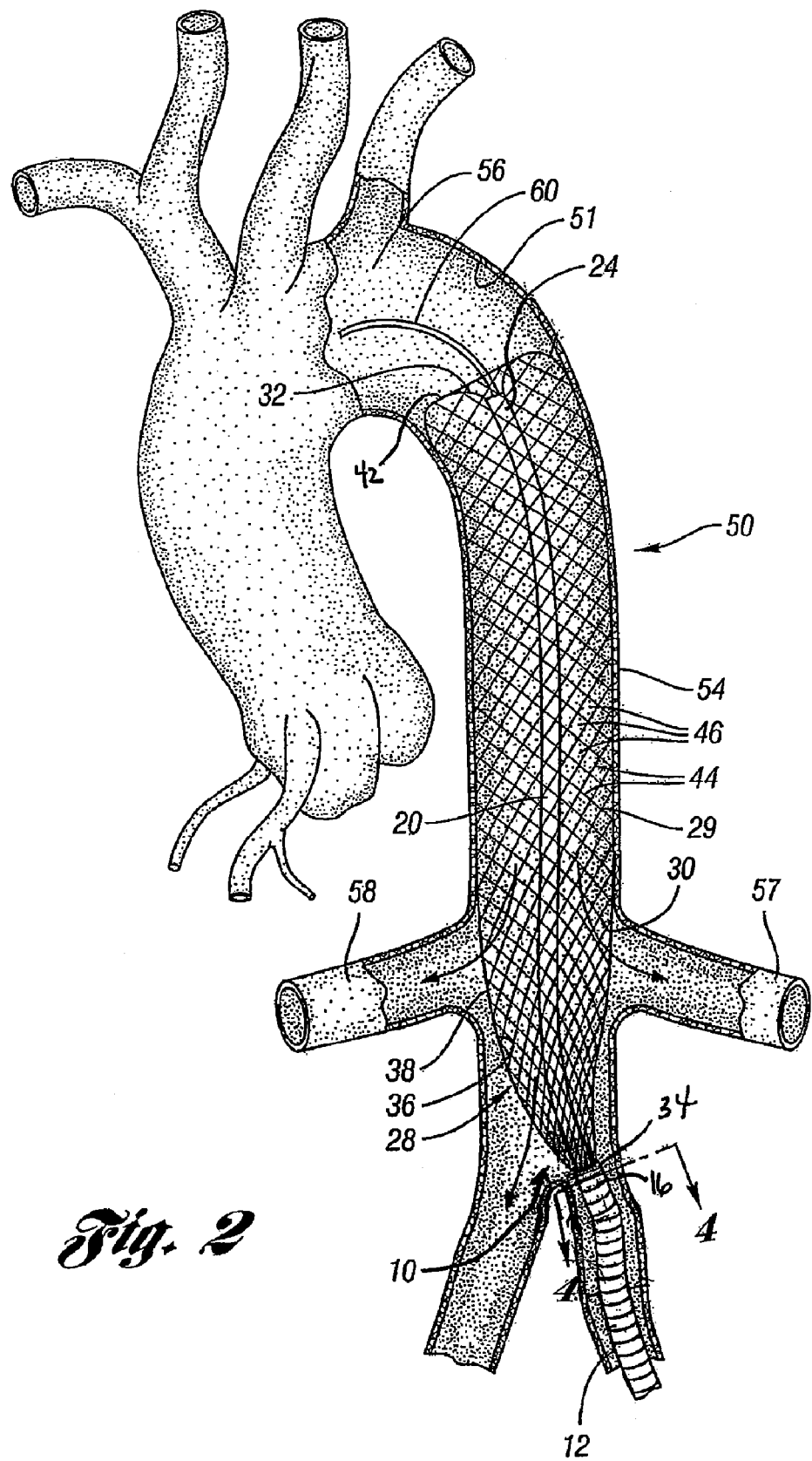
FIG. 2 is a cutaway perspective view of an embolic protection device deployed within an aorta in accordance with an embodiment of the present invention.

In this embodiment, the filter portion 28 includes a flexible filter body 30 movable from an everted state to a generally non-everted state. As shown in FIGS. 1a-c, the filter body 30 extends from a first end 32 attached to the distal end 24 of the inner catheter 20 to a second end 34 attached to the distal end 16 of the outer catheter 12. In a preferred embodiment, the filter portion 28 is compressed within the distal end 16 of the outer catheter 12, defining the everted state. Preferably, as the filter portion 28 moves to the generally non-everted state, i.e., extends distally from the distal end 16 of the outer catheter 12, the filter portion 28 radially expands to engage the filter body 30 with an enclosing body vessel wall. This is discussed in more detail below with reference to FIGS. 2 and 3 as the expanded, generally non-everted deployed state is best illustrated in FIGS. 2 and 3.

FIG. 1a illustrates an everted state for insertion and removal of the device 10 within a patient's body vessel. In the everted state of FIG. 1a, the inner catheter 20 is proximally disposed within the lumen 18 of the outer catheter 12, the distal end 24 of the inner catheter 20 being arranged proximal to the distal end 16 of the outer catheter 12. In the everted state, the filter body 30 is everted, i.e., rolled inwardly and proximally, through the distal opening 17 of the outer catheter 12 and through a distal portion of the lumen 18 of the outer catheter 12. The inner wall 13 of the outer catheter 12 compresses the everted filter portion 28, defining a collapsed, everted state. Thus, the filter body 30 extends proximally from the second end 34 attached to the distal end 16 of the outer catheter 12 to the first end 32 attached to the distal end 24 of the inner catheter 20, defining an everted cavity or concave region 31 within the distal end 16 of the outer catheter 12.

In this embodiment, the filter body 30 includes an interior surface 36 and an exterior surface 38. In the everted state, the interior surface 36 faces the inner wall 13 of the outer catheter 12 and the exterior surface 38 defines the everted cavity 31 in fluid communication with the lumen 26 of the inner catheter 20. As illustrated in FIG. 1a, the length of the everted cavity 31 is greatest in the everted state, i.e., the filter portion 28 has the greatest degree of eversion in the everted state.

The everting nature of the filter portion 28 may be further understood with reference to a common article of clothing, a sock. A sock may be removed, allowed to hang toe downward, a hand inserted within the interior, the distal toe region pinched with fingers from within, and the pinched region pulled upward, forming an everted toe region which is pulled inside out to form an exterior distal cavity or dimple near the closed end of the sock. The open end of the sock has a proximal opening bounded by a proximal mouth region. The degree of eversion of the sock may be increased by moving the pinched region upward or the open end downward, increasing the amount of material within the distal exterior cavity. The terms filter sock or roll sock may be used interchangeably with filter portion 28 in describing and claiming the present invention.

In this embodiment, the outer and inner catheters 12, 20 are movable relative to one another to move the filter portion 28 to a generally non-everted state. For example, the outer catheter 12 may be moved proximally relative to the inner catheter 20 to unroll the filter portion 28 from the everted state. In another example, the inner catheter 20 may be moved distally relative to the outer catheter 12 to unroll the filter portion 28 from the everted state, or both the outer and inner catheters 12, 20 may be moved proximally and distally, respectively, to unroll the filter portion 28 from the everted state.

FIG. 1b illustrates a partially everted state in which at least one of the outer and inner catheters 12, 20 is moved relative to the other to move the inner catheter 20 distally within the lumen 18 of the outer catheter 12. In a partially everted state, the distal end 24 of the inner catheter 20 remains proximal to the distal end 16 of the outer catheter 12 and the filter body 30 maintains its everted shape. However, the degree of eversion is smaller than in the everted state, i.e., the length of the everted cavity 31 in a partially everted state is shorter than the length of the everted cavity 31 in the everted state of FIG. 1*a*. Thus, the length of the everted cavity decreases with decreasing eversion.

As illustrated in FIG. 1*b*, in a partially everted state, a first portion of the interior surface 36 of the filter body 30 faces the inner wall 13 of the outer catheter 12 and a second portion of the interior surface 36 faces a third portion of the interior surface 36. Further, in a partially everted state, a first portion of the exterior surface 38 of the filter body 30 defines the everted cavity 31 and a second portion of the exterior surface 38 of the filter body 30 faces the interior of a body vessel when disposed within a patient's body vessel.

FIG. 1*c* illustrates the filter portion 28 in a generally non-everted state in which the inner catheter 20 is extended through the distal opening 17 of the outer catheter 12 to unroll the everted filter portion to a generally non-everted state. FIG. 1*c* is merely illustrative of the relative positioning of the filter portion 28 in relation to the inner and outer catheters 20, 12 in a generally non-everted state. FIG. 1*c* does not illustrate the generally non-everted filter portion 28 in the preferred expanded state as later shown and described with reference to FIGS. 2 and 3. In the generally non-everted state of FIG. 1*c*, the filter body 30 extends distally from the second end 34 attached to the distal end 16 of the outer catheter 12 to the first end 32 attached to the distal end 24 of the inner catheter 20 such that the filter body 30 no longer defines an everted cavity 31. In this embodiment, the filter body 30 extends from the second end 34 and curves inward and proximally toward the first end 32, defining a proximally facing concave surface 42 adjacent the attachment point of the first end 32 to the distal end 24 of the inner catheter 20.

Further illustrated in FIG. 1*c*, in the generally non-everted state, the interior surface 36 of the filter body 30 defines the interior 29 of the filter body 30. In the generally non-everted state, the interior 29 of the filter body 30 is in fluid communication with the lumen 18 of the outer catheter 12 such that the inner catheter 20 passes though the lumen 18 and the distal opening 17 of the outer catheter 12 and through the interior 29 of the filter body 30. The interior surface 36 thus faces the outer wall 21 of the inner catheter 20 and the exterior surface 38 faces the interior of a body vessel when disposed within a patient's body vessel.

The term "generally non-everted" includes the embodiment of FIG. 1*c*, wherein the filter body 30 no longer defines an everted cavity 31, but wherein a very small portion of the filter body 30 curves inward and proximally, thus defining the proximally facing concave surface 42. The term "generally non-everted" further includes embodiments such as those illustrated in FIGS. 2 and 3, wherein the filter body 30 does define an everted cavity 31, but wherein the everted cavity is substantially smaller than in the everted state of FIG. 1*a* and the partially everted state of FIG. 1*b*, such that the filter body 30 is capable of engaging the body vessel wall and performing its intended function, i.e., preventing downstream flow of emboli or thrombi.

In both the everted and non-everted states of FIGS. 1*a* and 1*c*, respectively, the distal ends 16, 24 of respective outer and inner catheters 12, 20 are longitudinally separated by a distance 40 which is approximately the length of the filter body 30. The term "approximately the length of the filter body 30" includes a length equal to the length of the filter body 30 less the very small portion of the filter body 30 which either curves inward and proximally near the first end 32 in the non-everted state (i.e., the proximally facing concave surface 42), or curves inward and proximally near the second end 34 in the everted state (FIG. 1*a*), give or take the difference in length between the filter body 30 in the collapsed state and the filter body 30 in the expanded state. The distance 40 is thus substantially equal to the length of the everted cavity 31 in the everted state.

FIGS. 2 and 4 show an embolic protection device 10 deployed within a patient's aorta 50 in an expanded, generally non-everted deployed state. In this embodiment, the device 10 is inserted in the collapsed, everted state into the aorta 50 in a retrograde fashion. Preferably, this is done through a peripheral arterial access, such as the femoral artery or subclavian artery, using the Seldinger technique or an arterial cutdown. Accordingly, the outer and inner catheters 12, 20 should have a length sufficient to reach from the arterial access point where the device 10 is inserted to the ascending aorta 56 of the patient. For femoral artery deployment, the outer and inner catheters 12, 20 preferably have a length of about 80-120 cm. The inner catheter 20 is preferably longer than the outer catheter 12 by about at least the length of the filter body 30 in the expanded, generally non-everted state such that the proximal ends 14, 22 of both the outer and inner catheters 12, 20, respectively, are accessible from outside the patient's body to control the movement of the outer and inner catheters 12, 20 relative to one another.

In this embodiment, the position of the device 10 may be monitored using fluoroscopy or ultrasound. Appropriate markers, which may include radiopaque markers and/or sonoreflective markers, may be located on the distal ends 16, 24 of the outer and/or inner catheters 12, 20, and/or the filter portion 28 to enhance imaging and to show the position of the device 10 and the deployment state of the filter portion 28. As shown in FIG. 2, the device 10 is positioned within the descending thoracic aorta 54 proximal to a treatment site near the ascending aorta 56. The outer and inner catheters 12, 20 are movable relative to one another to deploy the filter portion 28 to the expanded, generally non-everted state proximal to the treatment site.

In this embodiment, the filter portion 28 is made of an expandable fine mesh material configured to expand to conform to the diameter of the body vessel. Thus, the diameter of the filter portion 28 in the collapsed, everted state is smaller than the diameter of the filter portion 28 in the expanded, generally non-everted state. The mesh filter portion 28 has a cylindrical geometry in the generally non-everted deployed state which includes an open region at the second end 34 and an enclosed region extending from the second end to the first end 32. In the generally non-everted state, the second end 34 is attached to and extends distally from the distal end 16 of the outer catheter 12, thus defining the open region through which the lumen 18 of the outer catheter 12 fluidly communicates with the interior 29 of the filter portion 28. The filter body 30 extends distally from the second end 34 and curves inwardly and proximally toward the first end 32 attached to the distal end 24 of the inner catheter 20, thus defining the proximally facing concave surface 42. The proximally facing concave surface 42 extends from the portion of the filter body 30 which engages the body vessel wall 51 toward the first end 32 attached to the distal end 24 of the inner catheter 20.

In this embodiment, the filter portion 28 may be attached to the inner and outer catheters 20, 12 by any suitable means in the art. For example, the filter portion 28 may be thermally or adhesively bonded to each of the inner and outer catheters 20,

12, on either the inside or outside of the inner and outer catheters 20, 12. Alternatively, the filter portion 28 may be an integral part of one of the inner and outer catheters 20, 12. For example, one of the inner and outer catheters 20, 12 may be formed from an inner layer of braided wire and an outer layer of polymer. The filter portion 28 may be an extension of the braided wire of one of the inner and outer catheters 20, 12 without the surrounding outer polymer layer. The filter portion 28 may be attached to the other one of the inner and outer catheters 20, 12 via thermal or adhesive bonding, or any other suitable means.

In this embodiment, the mesh material making up the filter portion 28 includes a plurality of elements 44, such as wires, fibers, or strands, which can be used to form the mesh material through a variety of methods, for example, braiding, knitting, weaving, helically winding, and counterwinding. The mesh material can be fused at some or all of the element 44 intersection points. The mesh material can also be electrospun, and formed of sheet or film having holes formed by laser drilling, punching dissolving components selectively, and the like. The elements 44 can be formed of material such as wire, which can be metallic or polymeric wire. The wire may be substantially circular in cross section or may have any number of square, rectangular or irregular cross sectional profiles.

The mesh material is formed such that the diameter of the filter portion 28 can expand or contract while maintaining its generally cylindrical geometry. To facilitate deployment of the device 10, the filter portion 28 is preferably biased to expand. However, when contracted, the cylindrical geometry is everted and provides a smaller profile during insertion and removal of the device 10 and facilitates delivery of the device 10 through the stenosis. The elements 44 may be comprised of any suitable material such as a superelastic material, stainless steel wire, cobalt-chromium-nickel-molybdenum-iron alloy, or cobalt-chrome alloy. Alternatively, the elements 44 may be formed of a synthetic material. For example, Nylon, Dacron, Thorolon, or ePTFE may be used. The fine mesh material of the filter portion 28 may be a woven or knitted fabric such as Dacron polyester or nylon mesh, or other textile fabrics, or it may be a nonwoven fabric, such as spun bonded polyolefin or ePTFE or other nonwoven materials. The fine mesh material of the filter portion 28 may be woven, knitted or otherwise formed from monofilament or multifilament fibers. The mesh material of the filter portion 28 may also be a fine wire mesh or a combination of wire and textile fibers. Depending on the application, the mesh material may include multiple layers or a composite mesh of elements 44, such as a nano-fiber mesh. Alternatively, the fine mesh material may be an open cell foam material.

Further, it is understood that the elements 44 may be formed of any other suitable material that will result in a flexible everting geometry, such as shape memory alloys. The mesh material is preferably self-expanding. The self-expanding mesh material can be formed totally or in part from self-expanding Nitinol, Elgiloy, titanium, or stainless steel wires and the like, and combinations thereof. The self-expanding mesh material can also be formed of engineering polymers, for example, liquid crystal polymer, PEEK, polyamide, polyester, and the like. A preferred mesh material is formed of Nitinol wires, which can be heat set to the desired expanded shape. The mesh material can preferably be heat set to a desired bias shape using any suitable method known in the art. In another example, the mesh material is highly elastic, and preformed by mechanical overstress to the desired expanded shape. The mesh material may be made partly or totally radiopaque by means of plating, core wires, tracer wires, or fillers that have good x-ray absorption characteristics compared to the human body.

In this embodiment, the mesh material includes openings 46 between the elements 44 that are large enough to allow the flow of blood therethrough, but small enough to prevent the passage of emboli or thrombi therethrough. Accordingly, the elements 44 may be configured such that the openings 46 between the elements 44 are between about 1-200 micrometers. The preferred opening or pore size of the mesh filter body 30 depends on the specific application and whether to prevent the passage of macroemboli only or macroemboli and microemboli. In most cases the pore size of the mesh filter body 30 will preferably be in the range of about 1-200 micrometers. For preventing the passage of macroemboli only, the pore size of the mesh filter body 30 will preferably be in the range of about 50-200 micrometers. For preventing the passage of macroemboli and microemboli, the pore size of the mesh filter body 30 will preferably be in the range of about 1-100 micrometers. In other applications, such as for treating thomboembolic disease, a larger pore size, e.g. up to 1000 micrometers or larger, may be useful. A filter body 30 having openings 46 of these sizes will allow blood cells to pass through the openings 46 while larger emboli or thrombi are restrained by the elements 44 from traveling downstream within the body vessel. In some embodiments, a combination of filter materials having different pore sizes may be used.

Alternatively or additionally, the mesh material of the filter portion 28 may be made of or coated with an adherent material or substance to capture or hold embolic debris or thrombi which comes into contact with the filter portion 28. Suitable adherent materials include, but are not limited to, known biocompatible adhesives and bioadhesive materials or substances, which are hemocompatible and non-thrombogenic. In a preferred embodiment, only the upstream side of the elements 44 of the proximally facing concave surface 42 of the filter portion 28 is coated with the adherent material to positively capture the embolic debris which comes in contact with the proximally facing concave surface 42 of the filter portion 28.

Referring to FIGS. 2 and 4, the filter portion 28 is positioned proximal to a medical surgical or treatment site, wherein the filter portion 28 is configured to move to the expanded, generally non-everted state to engage the body vessel wall. In this embodiment, the expanded filter portion 28 includes a cylindrical geometry adapted to span the diameter of the patient's body vessel, such that the filter portion 28 is radially biased against the wall of the vessel. An elongate medical instrument 60, such as a third catheter, is insertable through the lumen 26 of the inner catheter 20 in order to perform a medical procedure upstream of the filter portion 28. If any embolic materials are dislodged during the medical procedure, the enclosed region of the filter portion 28 prevents the embolic materials from traveling downstream through the body vessel and into surrounding vessel branches. The openings 46 defined by the elements 44 making up the porous mesh material of the filter portion 28 allow blood cells to flow downstream through the body vessel and into surrounding vessel branches. Thus, in the embodiments of FIGS. 2 and 3, the filter portion 28 permits blood flow to continue to the left and right renal 57, 58 and the abdominal aorta, yet prevents emboli or thrombi from entering into the left and right renal 57, 58 and the abdominal aorta.

After the medical procedure has been performed, the elongate medical instrument 60 is withdrawn from within the inner catheter 20 and the patient's body vessel. In this embodiment, the outer and inner catheters 12, 20 are movable relative to one another to roll or evert the filter portion 28 back into its collapsed, everted state for removal of the medical device 10. Preferably, as the filter portion 28 is manipulated into its collapsed, everted state, the everted cavity 31 swallows or captures the restrained emboli or thrombi within the outer catheter 12 for removal from the patient's body vessel. The medical device 10 is then withdrawn from within the patient's body vessel.

Referring to FIG. 3, a device 10 in accordance with an embodiment of the present invention is positioned within the patient's aorta directly at the branch site of the left and right renal 57, 58. In this embodiment, a plurality of markers 70*a* and 70*b* is integrated into the filter portion 28 to help the physician monitor the deployment of the filter portion 28. The markers are preferably tungsten loaded nylon. In this embodiment, the markers 70*a* are preferably positioned in an axial direction to mark the renal branch site and the markers 70*b* are preferably positioned perpendicular to the axial direction to follow the deployment of the expandable filter portion 28.

FIG. 5 shows a cross-sectional view of the device 10 in FIG. 3 taken along line 5-5, along the proximally facing concave surface 42 of the filter portion 28. As illustrated, in the region defined by the proximally facing concave surface 42, the elements 44 engage the body vessel wall 51 and traverse the lumen of the body vessel towards the distal end 24 of the inner catheter 20, thus defining the enclosed region of the filter portion 28.

Figure 6:
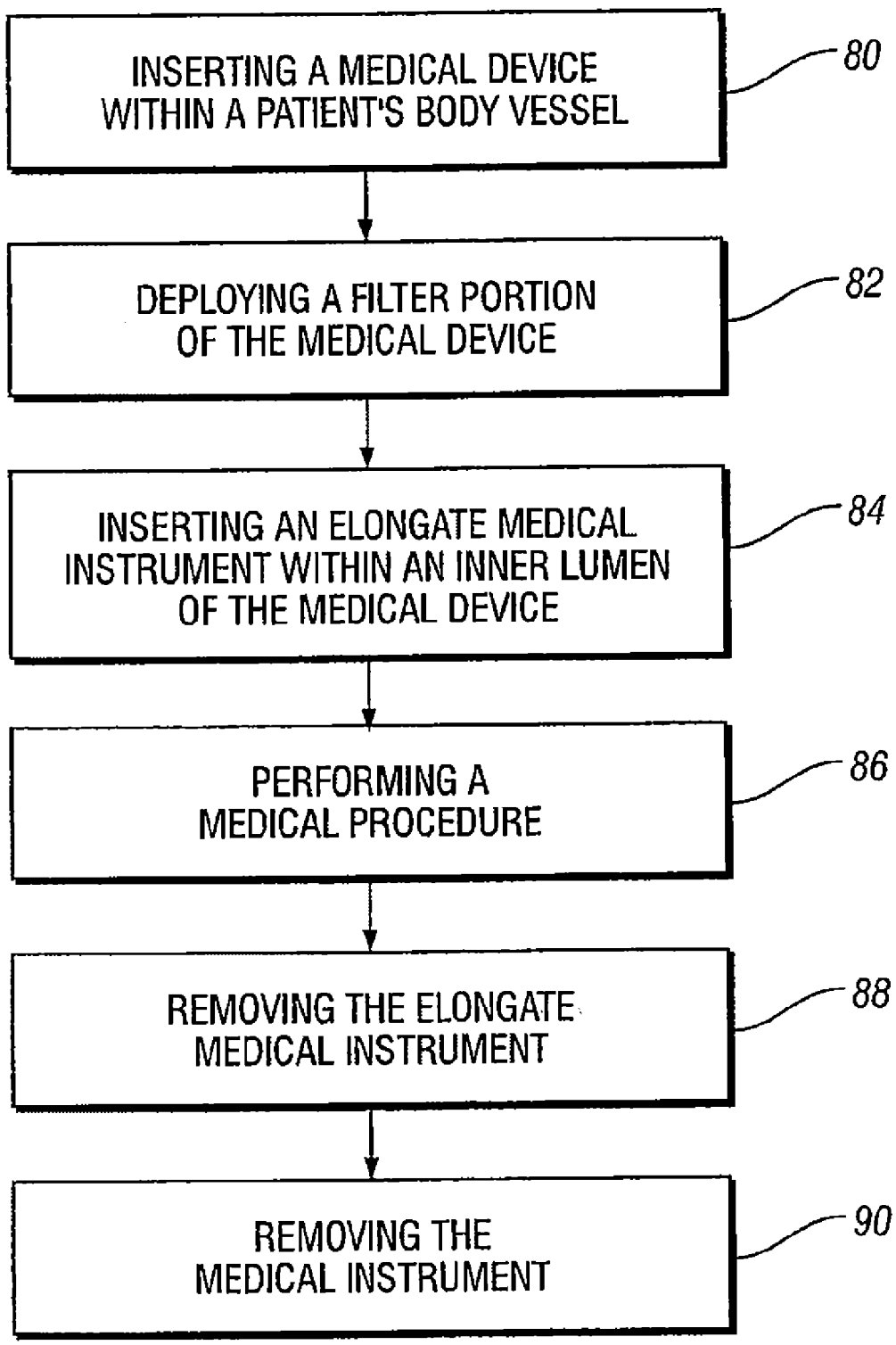
FIG. 6 is a flow chart illustrating a method of embolic protection during a medical procedure in a patient's body vessel.

Referring to FIG. 6, a method of embolic protection during a medical procedure is provided. The method includes inserting (80) a medical device 10, as discussed in the forgoing paragraphs, into an operative position within a body vessel of a patient. During insertion, the filter portion 28 is in the collapsed, everted configuration.

The filter portion 28 is deployed (82) to the expanded, generally non-everted configuration within the body vessel. Deploying the filter portion 28 includes moving the outer and inner catheters 12, 20 relative to one another such that the distal end 24 of the inner catheter 20 and the first end 32 of the filter portion 28 extend distally from the distal end 16 of the outer catheter 12.

An elongate medical instrument 60, such as a catheter, is inserted (84) within the lumen 26 of the inner catheter 20 via the proximal opening 23 of the inner catheter 20. The medical instrument 60 passes through the distal opening 25 of the inner catheter 20 and the first end 32 of the filter portion 28 to perform the medical procedure within the body vessel of the patient upstream of the filter portion 28. The filter portion 28 permits blood flow to surrounding vessels while preventing any dislodged emboli or thrombi from flowing downstream and entering surrounding vessels.

After the medical procedure is performed (86), the medical instrument 60 is removed (88) from within the inner catheter 20 and the body vessel of the patient. Thereafter, the medical device 10 is removed (90) from within the body vessel of the patient. Removing the medical device 10 includes moving the outer and inner catheters 12, 20 relative to one another to evert the filter portion 28 back into its collapsed, everted state, wherein the distal end 24 of the inner catheter 20 and the first end 32 of the filter portion 28 are arranged proximally within the outer catheter 12. Preferably, as the filter portion 28 is everted back into its collapsed everted state, emboli or thrombi are collected within the everted cavity 31 at the distal end 16 of the outer catheter 12 and removed with the medical device 10.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A medical device for embolic protection within a patient's body vessel, the medical device having a first lumen and a second lumen, the medical device comprising:
    an outer catheter having a proximal end and a distal end, the outer catheter having an outer lumen formed through the proximal and distal ends defining a proximal opening at the proximal end and a distal opening at the distal end of the outer catheter;
    an inner catheter movable within the outer catheter and having a proximal end and a distal end, the inner catheter having an inner lumen formed through the proximal and distal ends defining a proximal opening at the proximal end and a distal opening at the distal end of the inner catheter; and
    a flexible filter portion having a body extending from a first end to a second end, the first end being attached to the distal end of the inner catheter and the second end being attached to the distal end of the outer catheter, the outer catheter and the inner catheter movable relative to one another to move the filter portion between a collapsed state for delivery and removal of the device and an expanded state for engaging the filter body with a body vessel wall, the distal end of the inner catheter being arranged proximal to the distal end of the outer catheter such that the filter body is everted and defines a distal cavity within the distal end of the outer catheter in the collapsed state, the distal end of the inner catheter being movable distal to the distal end of the outer catheter such that the filter body is generally non-everted and defines a cylindrical body extending distally from the distal end of the outer catheter in the expanded state and enclosing a region configured to allow blood flow into surrounding vessel branches prevent emboli or thrombi from entering into the surrounding vessel branches, the distal ends of the outer catheter and the inner catheter being longitudinally separated by approximately the length of the filter body in the collapsed state and in the expanded state.

2. The medical device of claim 1, wherein the filter body includes an opening at the first end and a proximally facing concave surface adjacent the second end in the collapsed state, the proximally facing concave surface defining the distal cavity and the opening providing fluid communication between the inner catheter lumen and the distal cavity.

3. The medical device of claim 1, wherein the filter body includes an opening at the second end and a proximally facing concave surface adjacent the first end in the expanded state, the proximally facing concave surface defining an interior of the filter portion and the opening providing fluid communication between the outer catheter lumen and the interior of the filter portion.

4. The medical device of claim 3, wherein the inner catheter is disposed within the interior of the filter portion in the expanded state.

5. The medical device of claim 1, further comprising an elongate instrument movable longitudinally within the inner catheter lumen relative to the inner catheter and extendible through the proximal and distal openings of the inner catheter.

6. The medical device of claim 1, wherein the filter portion includes a plurality of elements defining a plurality of openings sized to allow blood cells to pass through the filter openings and prevent the passage of emboli.

7. The medical device of claim 1, wherein the filter portion includes a porous expandable mesh structure.

8. The medical device of claim 7, wherein the mesh structure is constructed from a material selected from the group consisting of polyester, nylon, Dacron, thorolon, ePTFE, stainless steel, nickel-titanium alloys, and cobalt-base alloys.

9. The medical device of claim 1, wherein the filter portion includes at least one radiopaque marker to assist in monitoring deployment of the filter portion.

10. The medical device of claim 1, wherein the device is configured to be positioned within the body vessel such that the filter portion in the expanded state is longitudinally disposed within the first lumen and transversely disposed relative to the second lumen, wherein the filter portion allows blood cells to pass through the first lumen and into the second lumen and prevents emboli from entering the second lumen.

11. A medical device for capturing emboli in a patient's body vessel, the medical device having a first lumen and a second lumen, the medical device comprising:
an elongate outer tubular member and an elongate inner tubular member movable within the outer tubular member, each of the outer and inner tubular members having a proximal end and a distal end and a lumen formed through the proximal and distal ends defining a proximal opening at the proximal end and a distal opening at the distal end; and
a flexible everting filter portion having a body extending from a first end to a second end, the first end being attached to the distal end of the inner tubular member and the second end being attached to the distal end of the outer tubular member, the filter portion movable between a collapsed insertion and removal configuration and an expanded deployed configuration, the filter portion being compressed in an everted state within the distal end of the outer tubular member in the collapsed configuration, the inner and outer tubular members being movable relative to one another to distally extend the filter portion from the outer tubular member, the filter portion being biased to expand radially outward to engage the filter body with an enclosing body vessel wall in the expanded configuration and to enclose a region configured to allow blood flow into surrounding vessel branches prevent emboli or thrombi from entering into the surrounding vessel branches.

12. The medical device of claim 11, wherein the first end of the filter portion attached to the distal end of the inner tubular member is arranged proximal to the second end of the filter portion attached to the distal end of the outer tubular member defining an everted distal cavity in the collapsed configuration.

13. The medical device of claim 11, wherein the first end of the filter portion attached to the distal end of the inner tubular member is arranged distal to the second end of the filter portion attached to the distal end of the outer tubular member defining a cylindrical distal extension of the outer tubular member in the expanded configuration.

14. The medical device of claim 11, wherein the filter portion includes an interior surface and an exterior surface, the interior surface facing an inner wall of the outer tubular member and the exterior surface defining an everted distal cavity within the distal end of the outer tubular member in the collapsed configuration, the interior surface defining an interior of the filter portion through which the inner tubular member extends and the exterior surface being configured to engage the body vessel in the expanded configuration.

15. The medical device of claim 11, wherein the filter portion includes a plurality of elements defining a plurality of openings sized to allow blood cells to pass through the filter openings and prevent the passage of emboli.

16. The medical device of claim 11, wherein the filter portion includes a porous expandable mesh structure constructed from a material selected from the group consisting of polyester, nylon, Dacron, thorolon, ePTFE, stainless steel, nickel-titanium alloys, and cobalt-base alloys.

17. The medical device of claim 11, further comprising an elongate instrument movable longitudinally within the inner tubular member lumen relative to the inner tubular member and extendible through the proximal and distal openings of the inner tubular member.

* * * * *

UNITED STATES PATENT AND TRADEMARK OFFICE
CERTIFICATE OF CORRECTION

| | |
|---|---|
| PATENT NO. | : 8,388,644 B2 |
| APPLICATION NO. | : 12/345127 |
| DATED | : March 5, 2013 |
| INVENTOR(S) | : Fred T. Parker |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 747 days.

Signed and Sealed this
Twenty-eighth Day of October, 2014

Michelle K. Lee
*Deputy Director of the United States Patent and Trademark Office*